(12) United States Patent
Zhanggui et al.

(10) Patent No.: US 8,722,725 B2
(45) Date of Patent: May 13, 2014

(54) CAFFEOYLQUINIC ACID DERIVATIVES CONTAINING NITROGEN, AND PREPARATION METHOD, PHARMACEUTICAL COMPOSITION AND USAGE THEREOF

(75) Inventors: Wu Zhanggui, Hangzhou (CN); Wei Wei, Zhejiang Province (CN)

(73) Assignee: Zhejiang Medicine Co., Ltd. Xinchang Pharmaceutical Factory, Zhejiang Province (CN)

( * ) Notice: Subject to any disclaimer, the term of this patent is extended or adjusted under 35 U.S.C. 154(b) by 288 days.

(21) Appl. No.: 12/532,763

(22) PCT Filed: Mar. 21, 2008

(86) PCT No.: PCT/CN2008/000562
§ 371 (c)(1),
(2), (4) Date: Feb. 11, 2010

(87) PCT Pub. No.: WO2008/116385
PCT Pub. Date: Oct. 2, 2008

(65) Prior Publication Data
US 2010/0144828 A1 Jun. 10, 2010

(30) Foreign Application Priority Data

Mar. 23, 2007 (CN) .......................... 2007 1 0086601
Mar. 20, 2008 (CN) .......................... 2008 1 0084391

(51) Int. Cl.
*C07D 295/185* (2006.01)
*C07C 235/40* (2006.01)

(52) U.S. Cl.
CPC .......... *C07C 235/40* (2013.01); *C07D 295/185* (2013.01)
USPC .............. 514/423; 514/533; 548/539; 560/84

(58) Field of Classification Search
None
See application file for complete search history.

(56) References Cited

U.S. PATENT DOCUMENTS

| | | | | |
|---|---|---|---|---|
| 2,918,477 | A * | 12/1959 | Cattapan et al. | 549/229 |
| 8,115,031 | B2 * | 2/2012 | Yates et al. | 564/189 |
| 2009/0234015 | A1 * | 9/2009 | Yates et al. | 514/613 |
| 2010/0144828 | A1 | 6/2010 | Wu et al. | |
| 2010/0311827 | A1 * | 12/2010 | Daneshtalab et al. | 514/466 |

FOREIGN PATENT DOCUMENTS

| | | | |
|---|---|---|---|
| CN | 1175411 | 3/1998 | |
| CN | 1415758 | 5/2003 | |
| CN | 1657601 | 8/2005 | |
| EP | 0159180 | 10/1985 | |
| EP | 0265071 | 4/1988 | |
| EP | 1200462 | 5/2005 | |
| JP | 2006-298802 | * 11/2006 | ............ C07C 279/14 |
| WO | 9809964 | 3/1998 | |
| WO | 2004052310 | 6/2004 | |
| WO | 2005118585 | 12/2005 | |
| WO | 2007030657 | 3/2007 | |
| WO | 2008098471 | 8/2008 | |
| WO | 2009046618 | 4/2009 | |
| WO | WO 2009/062200 | * 5/2009 | ............. A01N 37/10 |

OTHER PUBLICATIONS

"Human Immunodeficiency Virus Type 2." Published by the CDC, Oct. 1998.*
Kashman et al. J. Med. Chem. 1992, 35, pp. 2735-2743.*
Marcus et al., PubMed Abstract (Intervirology 45(4-6):260-6) 2002.*
Miles, Medline Abstract (Community Pract, vol. 78, Issue 8, pp. 292-294) Aug. 2005.*
Human Immunodeficiency Virus I from Merck manual, pp. 1-16. Accessed Aug. 27, 2009.*
Respiratory Viruses Introduction from Merck manual, pp. 1-2. Accessed Aug. 27, 2009.*
Acute Viral Hepatitis from Merck manual, pp. 1-8. Accessed Aug. 27, 2009.*
Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Ma et al. Bioorg. Med. Chem. 15 (2007), pp. 6830-6833.*

* cited by examiner

*Primary Examiner* — Alicia L Otton
(74) *Attorney, Agent, or Firm* — Daniel A. Thomson; Emerson Thomson Bennett, LLC

(57) ABSTRACT

The present invention provides caffeoylquinic acid derivatives and a method of preparing for the same, and also provides pharmaceutical compositions containing caffeoylquinic acid derivatives, and uses of caffeoylquinic acid derivatives in preparation of a medicament for the treatment or prophylaxis of virus diseases, in particular, uses of respiratory syncytial virus and hepatitis B virus, which has the characteristics of safety, high effectiveness and low toxicity.

16 Claims, No Drawings

CAFFEOYLQUINIC ACID DERIVATIVES CONTAINING NITROGEN, AND PREPARATION METHOD, PHARMACEUTICAL COMPOSITION AND USAGE THEREOF

FIELD OF THE INVENTION

The present invention relates to caffeoylquinic acid derivatives and a method for preparing the same, pharmaceutical composition containing the caffeoylquinic acid derivatives, and the use of the caffeoylquinic acid derivatives in preparation of a medicament for the treatment or prophylaxis of virus diseases.

BACKGROUND

Virus having highly infectivity is a kind of pathogen to severe harm human health and threatens human life, such as influenza virus, AIDS virus, SARS virus, hepatitis B virus, etc. The prevention of virus is mainly antiviral vaccine. But, conventional vaccines still could not effectively prevent and stop their outbreak and epidemic because these viruses are easy to change. Most of viruses are insensitive to antibiotic chemical medicine, which has become a very difficult problem in medical field at present. Some medicines such as medically exogenous interferon, interleukin-2, etc. could inhibit the virus replication and improve cell-mediated immune function of the organism, which have good therapeutic prospect but high cost and there still exists certain adverse reaction while using a large of amounts. However, clinical prevention and treatment with traditional Chinese medicines have unique effects, low toxic side effects, rich medicinal herbs resources, low costs, and could regulate global immune functions, inhibit virus replications, prevent cytopathic effects caused by virus, and improve clinical symptoms. So clinical prevention and treatment with traditional Chinese medicines are widely used for treating virus infective diseases, meanwhile exhibits unique advantages. In recent years, many people do different studies on anti-virus with traditional Chinese medicines from different angles and directions.

Caffeoylquinic acid compounds widely exist in plants, for example Chinese herbal medicines, fruits, vegetables, or so on. Dicaffeoylquinic acid (DCQA) also called as dicaffeoylquinic acid which belongs to dicaffeic acid ester of quinic acid. Dicaffeoylquinic acid as a kind of pharmacologically active ingredient has widely functional range, and possesses many effects, such as anti-virus (CN1087608; EP1008344; U.S. Pat. No. 6,331,565; US20020111382), antioxidation (CN1136434; YanRong Sun, JunXing Dong, et al., Bulletin of the Academy of Military Medical Sciences, 2002, 26(1): 39), improving immune function (CN1136434), anti-hepatic injury (CN1476842; YanRong Sun, JunXing Dong, et al., Bulletin of the Academy of Military Medical Sciences, 2002, 26(1): 39), anti-mutagenesis (Yoshimoto M., et al., Biosci Biotechnol Biochem, 2002, 66(11): 2336), etc. And DCQA has certain therapeutic effects on aspects of virus infective and cardiovascular diseases. Meanwhile Dicaffeoylquinic acid also has therapeutic effects on infection of hepatitis B virus (CN1087608; EP1008344; U.S. Pat. No. 6,331,565), AIDS virus (CN1087608; EP1008344; U.S. Pat. No. 6,331,565), coronavirus. It is also used for cosmetics (EP577516; U.S. Pat. No. 5,445,816).

Respiratory syncytial virus pneumonia is called as syncytial virus pneumonia in brief, it is a common interstitial pneumonia of child and is easy occurred in infant. Because maternal-transferred antibody cannot prevent from occurrence of infection, infants may shortly become ill after birth, but newborn baby is rare. It is infrequently reported that nosocomial infection results in outbreak in neonatal ward of maternity hospital. So far, there is still not particularly effective treatment and prevention solution though considerable progresses have been made in the study on RSV infection. Currently, only medicines used for chemotherapy are mainly ribavirin, and also comprise amantadine and arbidol hydrochloride. Other medicines such as human monoclonal antibody palivizumab (Synagis) and intravenous immunoglobulin (RSV-IGIV) have been registered and used and have good therapeutic effects but could not be widely used for clinic due to the high costs required in a periodic heal.

SUMMARY

It is an object of the present invention to provide novel caffeoylquinic acid derivatives and its preparation to make up for the above-mentioned deficiencies.

It is another object of the present invention to further provide pharmaceutical compositions comprising a therapeutically effective amount of the above compounds or salts or hydrates thereof and pharmaceutically acceptable carriers.

Furthermore, it is still another object of the present invention to further provide uses of caffeoylquinic acid derivatives in preparation of a medicament of the compounds or salts or hydrates thereof for the treatment or prophylaxis of virus diseases.

According to the present invention, it provides compounds of the general Formula (I) or salts or hydrates thereof,

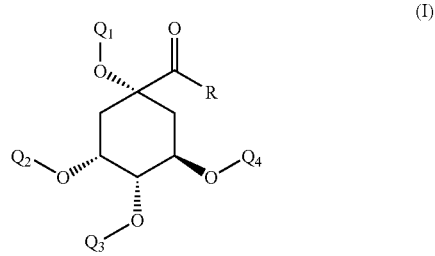

(I)

In the Formula:
R represents $NH_2$;
Or any mono-substituted or di-substituted $C_1$-$C_6$ alkylamino group with straight chain or branched chain;
Or any substituted $C_3$-$C_6$ naphthenic amino group;
Or any substituted $C_1$-$C_6$ aromatic amino group;
Or pyrrolidinyl group;
Or piperidyl group;
$Q_1$, $Q_2$, $Q_3$, $Q_4$ respectively represents H or the groups of the following Formula (II), and $Q_1$, $Q_2$, $Q_3$, $Q_4$ can not be H at the same time or $Q_1$, $Q_2$, $Q_3$, $Q_4$ can not be the group of the following Formula (II) at the same time.

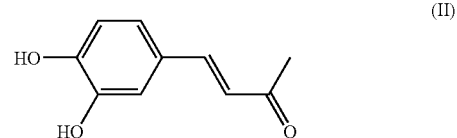

(II)

Wherein R is amino group, methylamino group, dimethylamino group, ethylamino group, isopropylamino group, pyrrolidinyl group, piperidyl group, anilino group, benzylamino group, para-tolyl amino group, cyclopropylamino group.

The compounds of the general Formula (I) or salts or hydrates thereof comprise the following compounds:

When R is cyclopropylamino group, it comprises six compounds, such as the compounds of Formula (1-1), (1-2), (1-3), (1-4), (1-5) and (1-6).

(1-1)

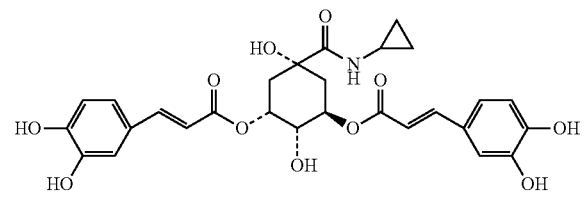

(1-2)

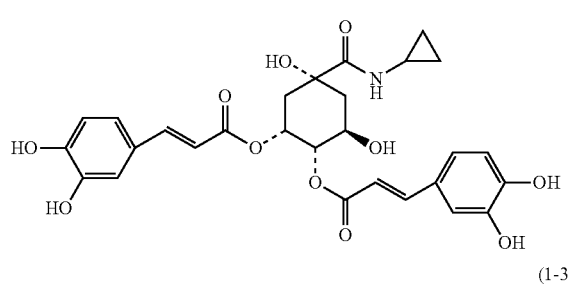

(1-3)

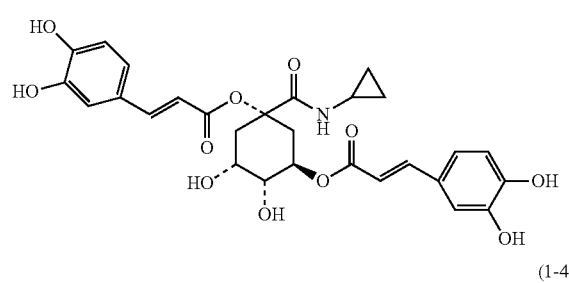

(1-4)

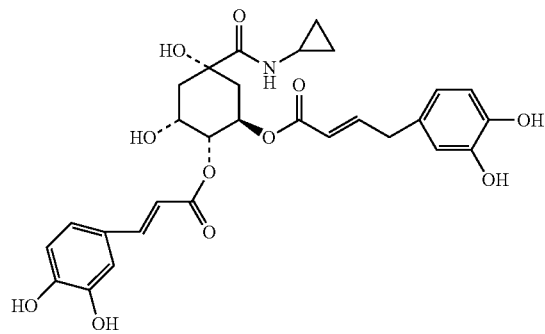

(1-5)

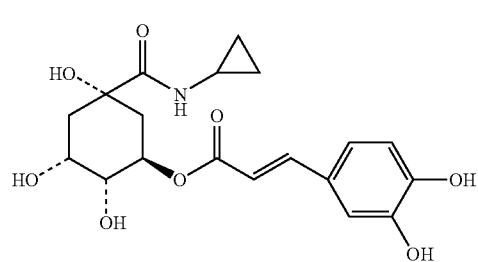

(1-6)

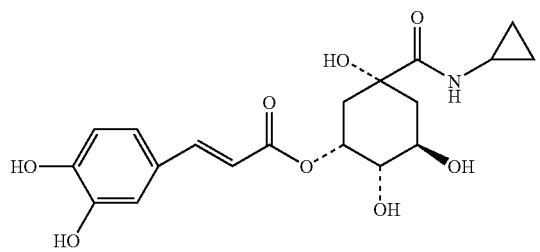

When R is pyrrolidinyl group, it comprises six compounds, such as the compounds of Formula (2-1), (2-2), (2-3), (2-4), (2-5) and (2-6).

(2-1)

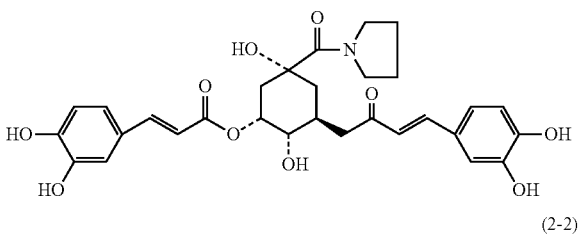

(2-2)

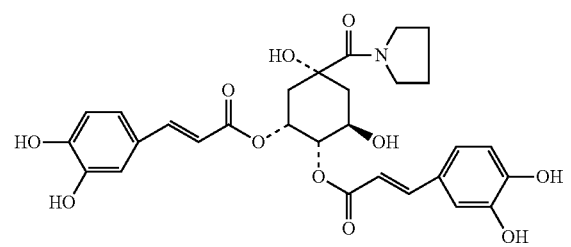

(2-3)

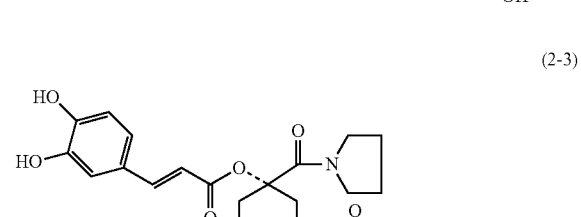

(2-4)

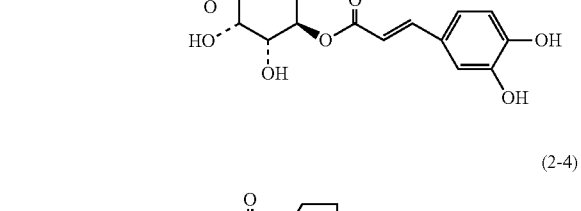

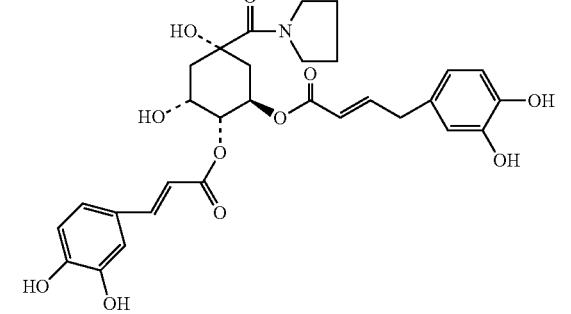

(2-5)

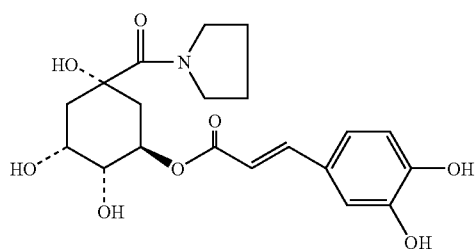

(2-6)

(3-4)

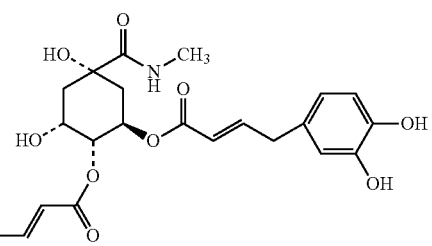

(3-5)

When R is methylamino group (NHCH$_3$), it comprises seven compounds, such as the compounds of Formula (3-1), (3-2), (3-3), (3-4), (3-5), (3-6) and (3-7).

(3-1)

(3-6)

(3-2)

(3-7)

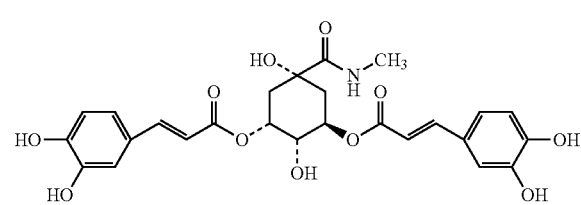

(3-3)

According to the present invention, it further provides pharmaceutical compositions comprising a therapeutically effective amount of at least one of the above compounds or salts or hydrates thereof and pharmaceutically acceptable carriers or excipients. Wherein the pharmaceutical composition is tablet, capsule, pill, oral liquid preparation, granule, powder, injection, implant or external preparation.

In general, the compound of the present invention is administrated in a therapeutically effective amount by any administration ways which are acceptable to play similar effects. A reasonable dose range is usually about 10 mg~1000 mg every day, preferably 200 mg every day. This depends on many factors, such as severity degree of treated disease, age of patient and their health status, efficacy of used compound, way and form of administration, symptom of administration and fancy and experience of relevant doctor. Ordinary technical persons skilled in the field of treating the diseases can determine a therapeutically effective amount of compounds of the present invention without many experiments and based on personal knowledge and contents disclosed in the present invention.

The compounds and one or more pharmaceutically acceptable carriers or excipients of the present invention may be added to the pharmaceutical composition with forms of unit dose. The pharmaceutical composition with form of unit dose may comprise conventional ingredients with regular proportions, containing or not containing active compounds or elements. And forms of unit dose may contain or adopt any reasonable effective amounts of active ingredients which correspond to predetermined dosage range of every day. The forms used for the pharmaceutical compositions may be tablet, capsule, pill, oral liquid preparation, granule, powder, injection, implant or external preparation.

According to the present invention, it further provides a method for preparing for the above compounds or the salts or hydrates thereof, wherein the method comprises the following steps:

(1) reacting quinic acid of Formula 4 with R to obtain a compound of Formula 3:

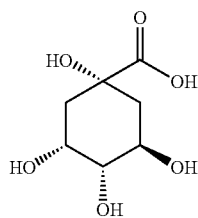

4

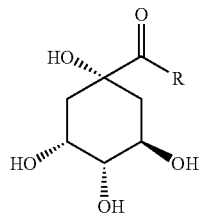

3

(2) and then reacting Formula 3 with Formula II to obtain a compound of the general Formula I

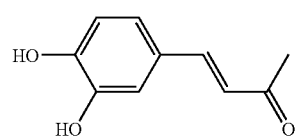

II

In the Formula:
R represents $NH_2$;
Or any mono-substituted or di-substituted $C_1$-$C_6$ alkylamino group with straight chain or branched chain;
Or any substituted $C_3$-$C_6$ naphthenic amino group;
Or any substituted $C_1$-$C_6$ aromatic amino group;
Or pyrrolidinyl group;
Or piperidyl group.

When R is cyclopropylamino group, pyrrolidinyl group or methylamino group, relevant compounds are synthesized according to the following synthetic route (Flow 1 and Flow 2) and synthetic technology:

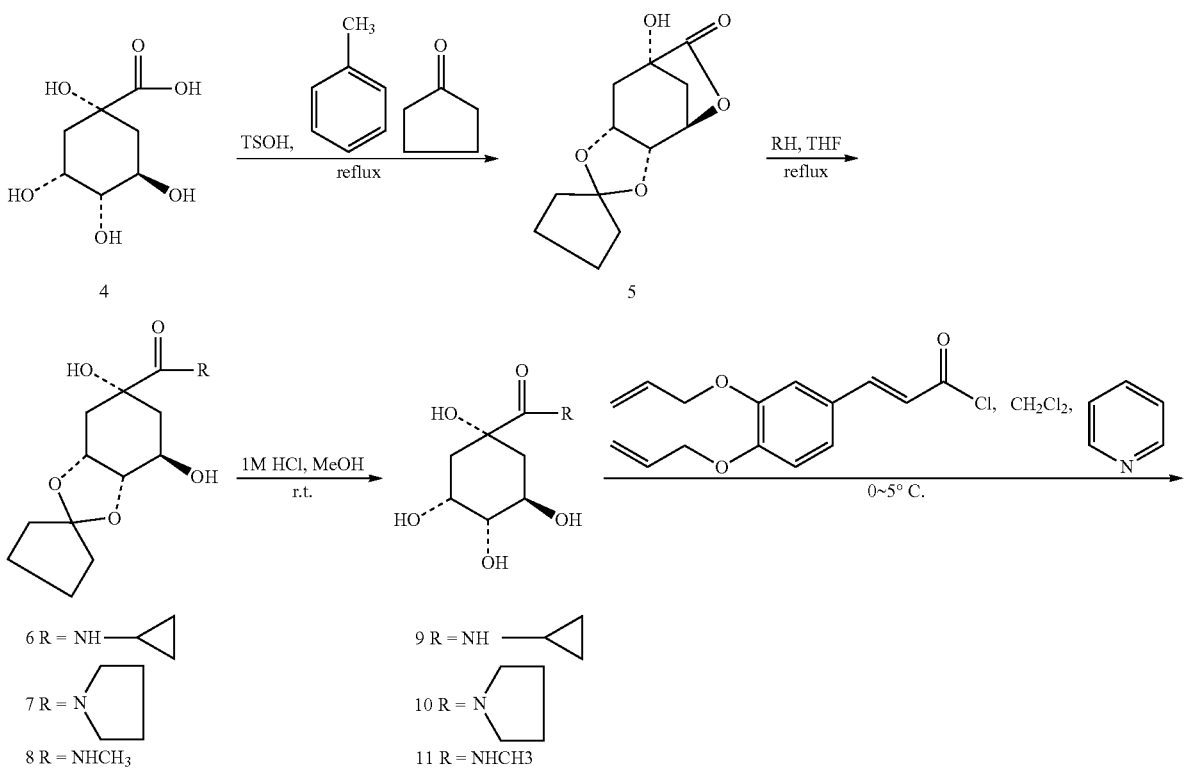

-continued
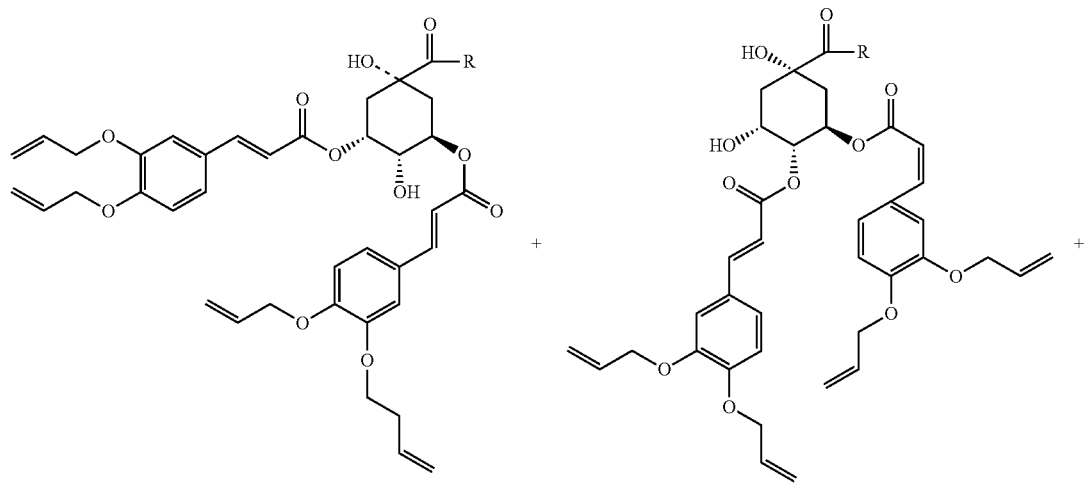
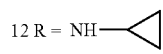
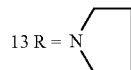
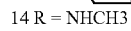
| THF
Pd[P(C6H5)3]4
Morpholine
reflux
(1-1) (2-1) (3-1)
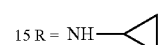
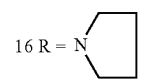
| THF
Pd[P(C6H5)3]4
Morpholine
reflux
(1-4) (2-4) (3-4)
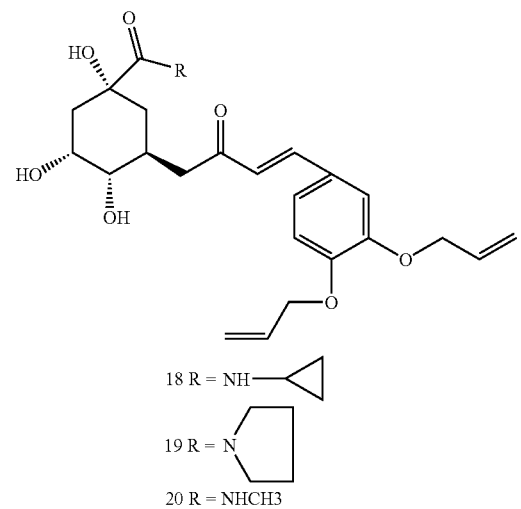
| THF
Pd[P(C6H5)3]4
Morpholine
reflux
(1-5) (2-5) (3-5)

Flow 2

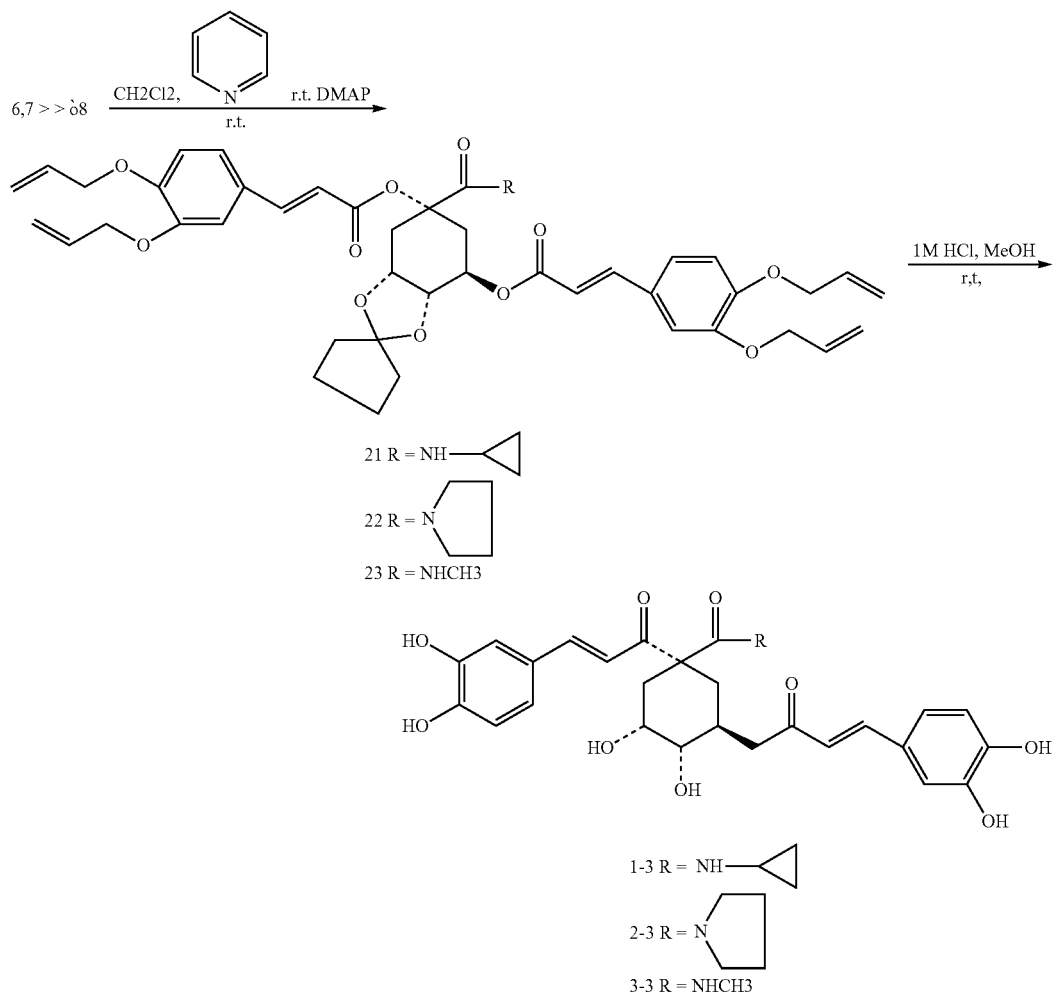

For the above-mentioned contents, except that the above-mentioned R is cyclopropylamino group, pyrrolidinyl group and methylamino group, a synthetic technology of the relevant compounds is carried out according to the above method, when R is other groups such as $NH_2$, any mono-substituted or di-substituted $C_1$-$C_6$ alkylamino group with straight chain or branched chain, any substituted $C_3$-$C_6$ naphthenic amino group, any substituted $C_1$-$C_6$ aromatic amino group, piperidyl group.

Quinic acid (4) reacts with cyclohexanone to make 3a,4a-position group of quinic acid form a ketal protection under catalysis of acids (such as TSOH, sulphuric acid, and so on), and by refluxing with toluene, and meanwhile 1β-position carboxyl group combines with 5β-position hydroxyl group to form lactone structure and obtain compound (5). Besides 3a,4a-position hydroxyl group of quinic acid may be formed a ketal protection by using cyclohexanone, also may be formed a ketal protection by using acetone. 1a-position carboxyl group is converted to amide structure to obtain compound (6), compound (7) and compound (8) etc. via opening loop of lactone structure of compound (5) by using amines such as rolicyprine or methylamine, etc. The solvent used may be THF, MeOH, EtoAc, etc. and the reaction temperature is about 40° C.~80° C. Under circumstances of acids, the protection groups of 3a,4a-position ketal of compounds (6), (7) or (8) are removed to obtain compounds (9), (10) or (11), etc. and the reaction temperature is about ~60° C. And then compounds (9), (10) or (11) respectively reacts of esterification with O-allyl caffeoyl chloride, wherein the solvents used are THF, EtOAc, $CH_2Cl_2$, or $CHCl_3$, and the bases used are $Et_3N$, pyridine, or $K_2CO_3$, and the reaction temperature is about −5° C.~5° C.; And then obtain compounds (12)~(20). The final step relates to de-protection of allyl group, because ally ether is stable under circumstances of common acids and bases, de-protection of allyl groups can not proceed under the circumstances.

But structures of allyl groups of compounds (12)~(20) could be easily removed under circumstances of removing allyl group, such as using $Rh(PPh_3)_3Cl/DABCO/EtOH$ or $Pd(PPh_3)_4/Morpholine/THF$, or so on, to obtain compounds (12)~(20).

According to the present invention, it further provides uses of caffeoylquinic acid derivatives in preparation of a medicament of the above compounds or salts or hydrates thereof for the treatment or prophylaxis of virus diseases. Wherein the viruses are respiratory syncytial virus, AIDS virus, hepatitis B virus.

The advantages and effects of the present invention are as follows: providing new caffeoylquinic acid derivatives to treat or prevent virus diseases, in particular respiratory syncytial virus and hepatitis B virus, the derivatives have characteristics of safety, high effectiveness and low toxicity. Wherein $IC_{50}$ of anti-respiratory syncytial virus of compound (2-1) in vitro is 1.37 μm/ml.

DETAILED DESCRIPTION

Hereafter, the present invention will be described specifically with reference to examples. The examples are given only for illustration of the technical solution of the present invention and should not be construed to limit the present invention.

Example 1

Synthesis of Compound (5)

Quinic acid of compound (4) (100 g), toluene (2 L), cyclohexanone (167 ml), TsOH (1 g) are reacted under refluxing for 15 h, and cooled to a room temperature to get a mixture. Then the above mixture is filtered and dried to obtain compound (5) 132 g with a white solid powder.
$^1$H-NMR (d-DMSO):1.348~1.702(m,10H), 1.848(dd, J=3.2,17.6,1H), 2.173(m,2H), 2.326(d,J=9,1H), 3.28(s,1H), 4.234(d,J=6.4,1H), 4.433(m,1H), 4.475(q,1H), 6.013(s,1H); $[M+1]^+$:255.

Example 2

Synthesis of Compound (6)

The above compound (5) (5 g), rolicyprine (6 ml) and DME (75 ml) are reacted under refluxing for 5.5 h and then the solvent is evaporated to get a mixture. The above mixture is separated and purified by the column chromatography, wherein chloroform and methanol are used as eluant. After the solvent is evaporated, compound (6) 4.7 g with white solid powder is obtained by drying. $[M+1]^+$: 312.

Example 3

Synthesis of Compound (7)

Compound (5) (5 g), pyrrolidine (2 ml), THF (50 ml) are reacted under refluxing for 6.5 h and then the solvent is evaporated to get a mixture. The above mixture is separated and purified by column chromatography, wherein acetidin and acetone are used as eluant. After the solvent is evaporated, compound (7) 5.3 g with light yellow solid is obtained by drying. $[M+1]^+$: 326.

Example 4

Synthesis of Compound (8)

After the compound (5) is dissolved in THF (100 ml), methylamine gas is put through for 4 h at a reflux temperature. After the solvent is evaporated, compound (8) of oily substance (9.4 g) is obtained and then is directly used for the following reaction.
$^1$H-NMR(d-DMSO):1.335(d,J=4.8, 2H); 1.442~1.760(m, 10H), 2.011(dd,J=19.2, 5.2, 1H), 2.595(d,J=4.4,3H), 3.762 (m,2H), 4.301(m,1H), 4.937(dd,J=15.2, 3.8, 1h), 5.152(s, 1H), 7.705(q,J=13.6, 4.4, 1H); [M+1]:286.

Example 5

Synthesis of Compound (9)

Compound (6) (3 g), methanol (30 ml) and 1M HCl (10 ml) are reacted under stirring at a room temperature for 2 h, and then the solvent is evaporated under a reduced pressure. After recrystallization by isopropyl alcohol, compound (9) 1.48 g with light yellow solid is obtained by drying. $[M+1]^+$: 232.

Example 6

Synthesis of Compound (10)

Compound (7) (3 g), methanol (30 ml) and 1M HCl (10 ml) are reacted under stirring at a room temperature, and then the solvent is evaporated under a reduced pressure. The above mixture is purified by the column chromatography wherein $CHCl_3$ and NaOH are used as eluant, and then obtain compound (10) 2 g with white solid. $[M+1]^+$: 246.

Example 7

Synthesis of Compound (11)

Compound (8) (8.5 g), methanol (85 ml), 1M HCl (25 ml) are reacted under stirring at a room temperature for 4 h and then the solvent is evaporated. After recrystallization by ethanol, compound (11) 5.5 g with white granulous solid is obtained by filtering and drying.
$^1$H-NMR(d-DMSO):1.681(m,4H), 2.594(d,J=5.2,3H), 3.228 (t,J=8.1H), 3.727(m,1H), 3.953(s,1H), 4.608(d,J=4.4, 1H), 4.837(d,J=5.2,1H), 5.109(d,J=3.2,1H), 5.419(s,1H), 7.727(d,J=4.4,1H); $[M+1]^+$:206.

Example 8

Synthesis of Compound (1-1)

Compound (9) (2.53 g), pyridine (35 ml) and $CH_2Cl_2$ (48 ml) are added to a three-mouth bottle. Under circumstance of protection of argon and temperature of 0~5° C., a solution of O-allyl caffeoyl chloride in $CH_2Cl_2$ (52 ml) (which is made of caffeic acid 7.4 g, refer to the preparation of Can. J. Chem, 75, 1997, 1783-94) is dropped into the three-mouth bottle to get a mixture. After dropping, the above mixture is reacted for 20 min. Then pH of the above mixture is adjusted to pH3~4 with 1M aqueous solution of HCl. $CH_2Cl_2$ layer is further washed to neutral with a saturated aqueous solution of NaCl and then dried with anhydrous $MgSO_4$. After filtering and evaporating the solvent, the oil substance is obtained. The oil substance is purified by the column chromatography, wherein acetidin and ligroin are used as eluant. After evaporating the solvent, the oil substance 1.17 g is obtained.

The oil substance is dissolved in THF (82 ml). Morpholine (5.7 ml) and $Pd(PPh_3)_4$ with a catalytic amount are added thereto to get a mixture. The above mixture is reacted under refluxing for 1 h and cooled to a room temperature. The reaction solution is washed to pH 3~4 with a saturated NaCl solution containing 1M HCl. THF layer is washed to neutral with saturated NaCl and then dried with anhydrous $MgSO_4$. After filtering and evaporating THF, the oil substance is obtained. The oil substance is purified by the column chromatography, wherein chloroform, methanol and formic acid are used as eluant. After evaporating the solvent, compound (1-1) 0.38 g with light yellow solid powder is obtained by drying.

$^1$H-NMR(d-DMSO):1.158(t,J=14.4,1H),1.690~2.055(m, 7H), 2.246~2.330(m,1H), 3.309(d,J=6.8,2H), 3.710(d,J=6, 2H), 4.075(m,2H), 4.831(dd,J=10.8,2.8,1H), 5.323(q,1H), 6.178(dd,J=20.8,5.2,2H), 6.715(t,J=16.8,2H), 6.883(q,2H), 7.013(s,2H), 7.394(dd,J=21.6,4.8,2H); [m+1]$^+$:556.

Example 9

Synthesis of Compound (14), (17), (20)

After the compound (11) is dissolved in pyridine (6 ml) and dichloromethane (10 ml), O-allyl caffeoyl chloride dissolved in $CH_2Cl_2$ (100 ml) is dropped thereto at temperature of 0~5° C. to get a mixture. After dropping, the above mixture is reacted for 20 min and 1 m HCl is added to the reaction. $CH_2Cl_2$ is washed to pH 4 with 1 m HCl and further washed to pH 7 with a saturated NaCl solution and then dried by anhydrous $MgSO_4$. After filtering and condensing, the oil substance is obtained. The oil substance is purified by the column chromatography, wherein acetidin and ligroin are used as eluant. And three components are obtained and collected.

Compound (14): 0.2 g, $^1$H-NMR(d-DMSO):1.159(m,1H), 1.841 (d,J=13.6,1H), 2.022(m,3H), 2.584(d,J=4.4,3H), 4.333 (s,1H), 4.407(m,9H), 4.966(dd,J=12,2,1H), 5.213(t,J=19.6, 4H), 5.369(d,J=17.6,4H), 5.601(s,2H), 5.890(d,J=5.2,1H), 5.983(m,4H), 6.484(t,J=25.5,2H), 6.946(t,J=14,2H), 7.153 (d,J=8,2H), 7.320(s,2H), 7.519(t,J=31.6,2H), 7.790(d,J=12, 1H); [M+1]$^+$:690, [M+Na]$^+$:712.

Compound (17):0.1, $^1$H-NMR(d-DMSO), 1158(m,1H), 1.891(m,3H), 2.144(d,J=11.6,1H), 2.631(d,J=4.4,3H), 4.196 (m,2H), 4.567(m,8H), 4.865(dd,J=11.6,3.2,1H), 5.255(t, J=4.4,4H), 5.354(m,6H), 5.970(m,4H), 6.462(d,J=16,2H), 6.950(q,2H), 7.162(q,2H), 7.311(t, J=4.4,2H), 7.528(dd, J=19.6,3.6,2H), 7.912(d,J=4.8,2H); [M+1]+:690, [M+Na]$^+$: 712.

Compound (20): 50 m, $^1$H-NMR(d-DMSO):1.764(q,1H), 1.870(q,3H), 2.619(d,J=4,3H), 4.022(q,1H), 4.154(s,1H), 4.615(m,6H), 5.255(d,J=11.4,2H), 5.395(d,J=17.6,2H), 6.005(m,1H), 6.518(d,J=16,1H), 7.007(d,J=8.4,1H), 7.233 (d,J=8,1H), 7.357(s,1H), 7.591(d,J=16.1H), 7.809(d,J=4.8, 1H); [M+1]$^+$:447.

Example 10

Synthesis of Compound (3-1)

Under circumstances of protection of argon, compound (14) (9.3 g), THF (150 ml), morpholine (45 ml) and a catalytic amount of Pd(PPh$_3$)$_4$ are reacted under refluxing for 1 h and cooled to a room temperature. THF layer is washed with a saturated NaCl solution containing 1M HCl till pH 3~4 and further washed to neutral with saturated NaCl; and then dried with anhydrous $MgSO_4$. After filtering and evaporating the solvent, the oil substance is obtained. The oil substance is purified by the column chromatography, wherein $CH_3Cl$, methanol and formic acid are used as eluant. After evaporating the solvent, the compound (3-1) with foamy solid powder is obtained by drying.

1H-NMR(d-DMSO):1.162~1.242(m,1H), 1.1846~2.131 (m,5H), 2.629(d,J=4,3H), 4.015(q,1H), 4.330(s,1H), 4.959 (d,J=9.2,1H), 5.383~5.634(m,1H), 6.161(t,J=14.4,29.2,2H), 6.731(q,3H), 7.060(t,J=34,4,2H), 7.809(d,J=4.8,1H); [m+1]+:530.

Example 11

Synthesis of Compound (3-4)

Under circumstances of protection of argon, Compound (17) (1.34 g), THF (21 ml), morpholine (7 ml) and a catalytic amount of Pd(PPh$_3$)$_4$ are reacted under refluxing for 1 h and cooled to a room temperature. THF layer is washed with a saturated NaCl solution containing 1M HCl till pH 3~4 and further washed to neutral with a saturated NaCl solution; and then dried with anhydrous $MgSO_4$. After filtering and evaporating the solvent, the oil substance is obtained. The oil substance is purified by the column chromatography, wherein $CH_3Cl$, methanol and formic acid are used as eluant. After evaporating the solvent, compound (3-4) with foamy solid powder is obtained by drying.

$^1$H-NMR(d-DMSO):1.756~1.967(m,4H), 2.621(d,J=4.4, 3H), 3.276(d3,6H), 4.141~4.199(m,1H), 4.816(d,J=12,1H), 5.346~5.468(m,3H), 178(dd,J=22,6.4,2H), 6.628~6.785(m, 2H), 6.925(t,J=15.6,2H), 7.020(s,2H), 7.879(d,J=4.8,1H); [m+1]$^±$:530.

Example 12

Synthesis of Compound (3-5)

Under circumstances of protection of argon, compound (20) (0.5 g), THF (56 ml), morpholine (2 ml) and a catalytic amount of Pd(PPh$_3$)$_4$ are reacted under refluxing for 0.5 h and cooled to a room temperature. THF layer is washed with a saturated NaCl solution containing 1M HCl till pH 3~4 and further washed to neutral with a saturated NaCl solution; and then dried with anhydrous $MgSO_4$. After filtering and evaporating the solvent, the oil substance is obtained. The oil substance is purified by the column chromatography wherein $CH_3Cl$, methanol and formic acid are used as eluant, and then obtain compound (3-5) with light yellow solid powder.

$^1$H-NMR(d-DMSO):1.785~1.983(m,4H), 0.69(d,J=4, 3H),4.066(q,1H), 4.177(s,1H), 4.626(t,J=9.6,1H), 6.317(d, J=16,1H), 6.807(d,J=4,1H), 7.005(d,J=8,1H), 7.088(s,1H), 7.521(d,J=8,1H), 7.879(d,J=4.4,1H), 8.216(s,1H); [M+1]$^+$: 367.

Example 13

Synthesis of Compound (1-3)

After compound (6) (0.4 g) and DMAP (0.1 g) are dissolved in $CH_2Cl_2$ (10 ml). Pyridine is added thereto, and then O-allyl caffeoyl chloride dissolved in $CH_2Cl_2$ (16 ml) is dropped thereto at a room temperature to get a mixture. After dropping a constant volume, the above mixture is reacted for 1 h, and pH is adjusted to about pH 3 with 2M HCl. After stirring at a room temperature for 2 h, filtering insoluble substances and separating from liquid, $CH_2Cl_2$ layer is washed to neutral with a saturated NaCl solution, and then dried with anhydrous $MgSO_4$. After filtering and evaporating $CH_2Cl_2$, the oil substance is obtained. The oil substance is purified by the column chromatography wherein acetidin and ligroin are used as eluant, and then obtain solid compound (1-3) 0.56 g. [M+1]$^+$:529.

Example 14

Synthesis of Compound (3-7)

After compound (11) is dissolved in pyridine (6 ml) and dichloromethane (10 ml), O-allyl caffeoyl chloride in $CH_2Cl_2$ solution (10 ml) is dropped thereto at a temperature of 0~5° C. to get a mixture. After dropping, the above mixture is reacted for 20 min, and 1 m HCl is added to the reaction. $CH_2Cl_2$ is washed to pH 4 with 1 m HCl and further washed to pH 7 with a saturated NaCl solution; and then dried with anhydrous $MgSO_4$. After filtering and condensing, the oil substance is obtained. The oil substance is purified by the column chromatography, wherein acetidin and ligroin are used as eluant.

Under circumstances of protection of argon, the above compound (product) (9.3 g), THF (150 ml), morpholine (45 ml) and catalytic amount of $Pd(PPh_3)_4$ are reacted under refluxing for 1 h and cooled to a room temperature. THF layer is washed with a saturated NaCl solution containing 1M HCl till pH 3~4 and further washed to neutral with a saturated NaCl solution; and then dried with anhydrous $MgSO_4$. After filtering and evaporating the solvent, the oil substance is obtained. The oil substance is purified by the column chromatography, wherein $CH_3Cl$, methanol and formic acid are used as eluant. After evaporating the solvent, the compound (3-7) with foamy solid powder is obtained by drying.

$^1$H-NMR(d-DMSO): 1.959(d,1H,J=12), 2.089(t,2H, J=10), 2.310(m,1H), 2.673(s,3H), 5.151(m, 1H), 5.515(m, 2H), 5.635(m,1H), 6.101(m,2H), 6.302(d,1H,J=4), 6.666(m, 9H), 7.377(m,3H), 7.822(d,1H,J=5.2), 7.846(s,1H), 8.220 (s,1H), 9.411 (s,6H); $[M+1]^+$:706.

Example 15

Inhibitory Effects on Anti-RSV In Vitro

Anti-RSV in vitro of the above partial compounds is tested. With Hep-2 cell (human laryngocarcinoma cell) as viral host, Hep-2 cytopathic extent caused by inhibiting RSV is measured and observed for 72 h. Half inhibition concentration ($IC_{50}$) of samples with respect to respiratory syncytial virus (RSV), its maximum of non toxicity concentration ($TC_0$) and half toxicity concentration ($TC_{50}$) of samples with respect to Hep-2 cell are respectively calculated by methods of Reed-Muench.

Test Material and Method:

Virus strains: RSV, Long strain

Sample treatment: before using, sample is prepared for a suitable concentration by being dissolved in DMSO, and is diluted to 3 times with a culture medium to form eight dilutions.

Positive control drug: ribavirin (RBV)

Test method: After Hep-2 cell is cultured in 96-well plate for 24 h, it is infected respiratory syncytial virus (RSV) (200TCID50 infective dose) and absorbed for 4 h to get a viral liquid. Then the viral liquid is discarded. The sample is added thereto according to the above eight dilutions, in the meantime cell control wells of positive drugs, normal cell control wells and viral control wells are set. The cytopathic extent (CPE) is observed for 72 h. Half inhibition concentration ($IC_{50}$) of samples with respect to respiratory syncytial virus (RSV), its maximum of no toxicity concentration ($TC_0$) and half toxicity concentration ($TC_{50}$) of samples with respect to Hep-2 cells are respectively calculated by method of Reed-Muench.

Concrete datum are shown in Table 1.

TABLE 1

Inhibitory Effect on Anti-RSV in Vitro

| Samples | $TC_{50}$ (µg/ml) | $TC_0$ (µg/ml) | $IC_{50}$ (µg/ml) |
| --- | --- | --- | --- |
| 1-1 | 111.11 | 37.04 | >111.11 |
| 1-3 | 12.35 | 4.12 | >12.35 |
| 2-1 | 111.11 | 37.04 | 1.37 |
| 2-3 | 12.35 | 4.12 | >12.35 |
| 3-1 | 64.15 | 37.04 | 16.25 |
| 3-3 | 111.11 | 37.04 | >111.11 |
| 3-4 | 37.04 | 12.35 | 7.13 |
| 3-5 | 37.04 | 12.35 | 7.13 |
| 3-7 | 64.15 | 37.04 | >64.15 |
| RBV | 333.33 | 111.11 | 1.37 |

Note:
RBV is a control substance, that is, Ribavirin

Example 16

Inhibitory Effect on Anti-HIV-1 IIIB/H9 Virus In Vitro

Anti-HIV-1 IIIB/H9 in vitro of the above partial compounds is tested. Half inhibition concentration ($IC_{50}$) of samples and half toxicity concentration ($TC_{50}$) of samples are respectively measured after culturing MT-4 cells, wherein the cell toxicity is measured by the method of CPE, and the inhibitory effects on HIV-1 IIIB of compounds are measured by method of measuring P24 antigen of cell culture supernatant.

Test Material and Method:

Virus strains: HIV-1 IIIB virus strain

Cell: T-lymphocyte MT-4

Sample treatment: before using, the sample is prepared for a suitable concentration by being dissolved in DMSO and then is further prepared for a cell culture medium.

Positive control drug: Zidovudine (AZT)

HIV-1 P24 antigen detection kit: Use products of BioMerieux Corporation in Holland.

Test method: The toxicity of drug in cell ($TC_{50}$ and $TC_0$) is measured by method of CPE. 100 µl cell is inoculated in 96-well plate at a density of $2 \times 10^5$ cells/ml. In the meantime, the medical solution 100 µl of 8 kinds of concentration of samples or positive drug zidovudine which are respectively diluted to 3 times are respectively added thereto, each of concentration is placed in 3 wells which are set to a cell control group. The above plates is cultured at the incubator of 37° C., 5% $CO_2$ and a saturated humidity. CPE Cells are observed at the fourth day (96 h) after adding drug, the cytopathic situation is recorded and $TC_{50}$ and $TC_0$ are calculated.

HIV-1 P24 antigen is measured by the method of ELISA. After counting the MT-4 cells, the cells are infected in the virus dose of 100TCID50 and absorbed for 1.5 h in the incubator of 37° C., 5% $CO_2$ and a saturated humidity. The cells are inoculated in a 96-well plate at the density of $2 \times 10^5$ cells/ml. After adding a diluted drug 100 ul/well, the culture of the plate is cultured at the incubator of 37° C., 5% $CO_2$ and a saturated humidity for 4 days (96 h). Cell supernatant is taken out and diluted in the ratio of 1:3000. HIV-1 P24 titer is measured according to the test steps provided by HIV-1 P24 antigen kit. Compared adding drug groups with viral control groups, half inhibition concentration ($IC_{50}$) of samples and half toxicity concentration ($TC_{50}$) of samples are respectively calculated Concrete datum are shown in Table 2.

TABLE 2

Inhibitory Effects on Anti-HIV-1 IIIB/H9 Virus in Vitro

| Samples | $TC_{50}$ (μg/ml) | $IC_{50}$ (μg/ml) |
|---|---|---|
| 2-1 | 32.08 | 1.18 |
| 3-1 | 32.08 | 1.83 |
| 3-4 | 32.08 | 0.93 |
| 3-7 | 32.08 | 1.02 |
| AZT | 20.00 | 0.0042 |

Note:
AZT is control substance, that is, zidovudine

Example 17

Inhibitory Effects on Anti-Hepatitis B DNA Virus (HBV) In Vitro

Anti-hepatitis (HBV) DNA virus in vitro of the above partial compounds is tested. human hepatoma carcinoma cells (Hep G2) in the 2.2.15 cell line are transfected by DNA cloning of hepatitis B virus (HBV), the inhibitory effect on cell toxicity and HBV DNA secretion are studied. Half inhibition concentration ($IC_{50}$) and half toxicity concentration ($TC_{50}$) of samples are measured, the inhibition ratio to HBV DNA in the 2.2.15 cell culture are obtained respectively.

Test Material and Method:

Virus strains: human hepatoma carcinoma cells (Hep G2) in 2.2.15 cell line are transfected by DNA cloning of hepatitis B virus (HBV).

Sample treatment: the sample is prepared for a suitable concentration by being dissolved in DMSO and preserved at 4° C. before using. When using, the required concentration is prepared by using a 2.2.15 cell culture medium.

Positive control drug: Lamivudine (3TC)

Test method: The sample is prepared for a 20 mg/ml mother liquor, and is further prepared for a required concentration by using a 2.2.15 cell culture medium. Then the above solution is diluted to 5 times from 200 μg/ml with the culture medium to form eight kinds of concentrations. The above solution is added to a 96-well cell plate, each of concentration is placed in 3 wells, and the medical solution with the same concentration is changed every 4 days. Cell control group without drug is set to observe cytopathic cell as a target, the cytopathic cell is observed under a microscope for 8 days, wherein full destruction is about 4; 75% of cytopathic cells are about 3; 50% of cytopathic cells are about 2; 25% of cytopathic cells are about 1; no cytopathic cells is about 0. Mean cytopathic extent and inhibition ratio of medical solutions for each concentration are calculated. Half toxicity concentration ($TC_{50}$) and its maximum of non toxicity concentration ($TC_0$) are respectively calculated by the method of Reed-Muench. According to the method of molecular cloning experimental technology, firstly the HBV DNA is extracted from 2.2.15 cells of medical solution of each concentration group and cell control groups, and then a dot blot hybridization and autoradiography of each sample are measured. After measuring IOD value or OD value of every hybridization dot, the inhibition ratio is calculated.

Concrete datum are shown in Table 3.

TABLE 3

Inhibitory Effects on Anti-hepatitis B DNA Virus (HBV) in Vitro

| Samples | Cell toxicity (μg/ml) | | HBV DNA | |
|---|---|---|---|---|
| | $TC_{50}$ | $TC_0$ | Inhibition ratio (%) | $IC_{50}$ (ug/ml) |
| 1-1 | 27.59 | 1.6 | — | |
| 1-3 | 4.69 | 1.6 | — | |
| 2-1 | 17.89 | 1.6 | — | |
| 2-3 | 3.58 | 0.32 | — | |
| 3-1 | 27.59 | 1.6 | — | |
| 3-3 | 3.58 | 0.32 | — | |
| 3-4 | 89.4 | 8 | — | |
| 3-5 | 89.44 | 8 | — | |
| 3-7 | >200 | >200 | 41.71 | |
| 3TC | | | 40.8~49.39 | |

Note:
3TC is control substances, that is, lamivudine.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A compound having Formula (I),

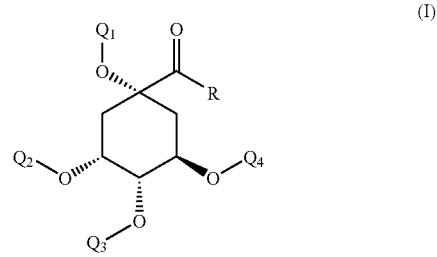

(I)

wherein R represents any $C_1$-$C_3$-alkyl amino group, wherein each instance of alkyl has a straight chain, or any $C_3$-naphthenic amino group, or pyrrolidinyl group; $Q_1$, $Q_2$, $Q_3$, $Q_4$ represents H or the group of the following Formula (II), with the proviso that Q1, Q2, Q3, and Q4 cannot all represent H at the same time and $Q_1$, $Q_2$, $Q_3$, and $Q_4$ cannot all represent the group of the following Formula (II) at the same time

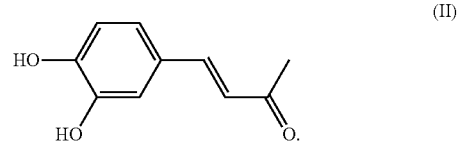

(II)

2. The compound according to claim 1, wherein R is chosen from the group consisting of methylamino group, ethylamino group, pyrrolidinyl group, and cyclopropylamino group.
3. The compound according to claim 1, wherein the compound is chosen from the group consisting of:
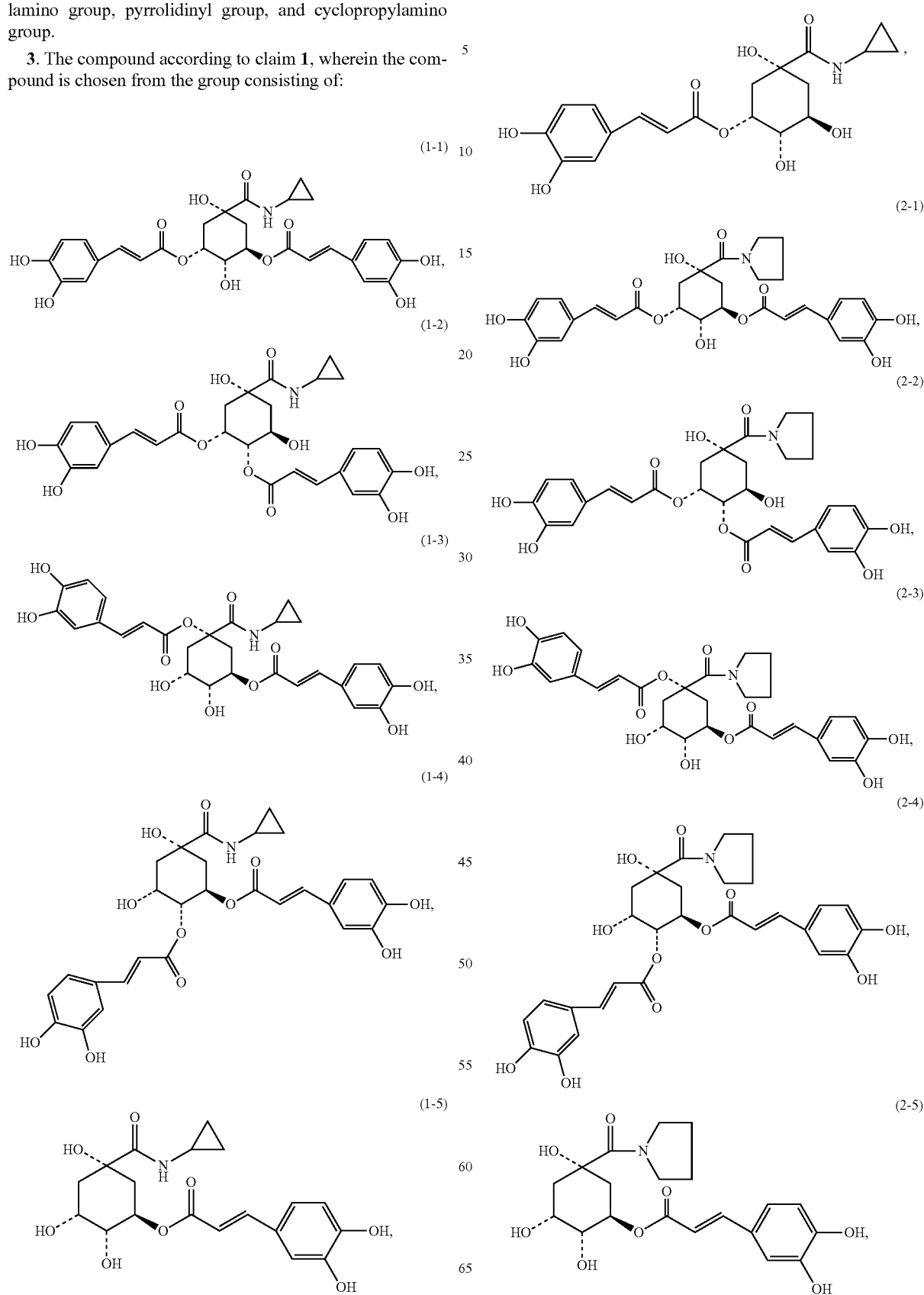

(2-6)
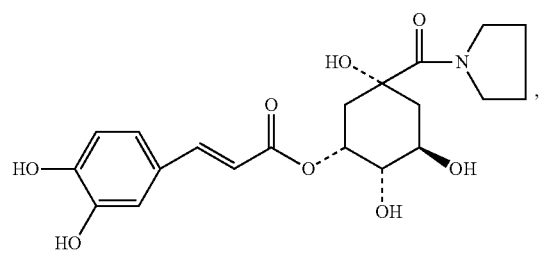

(3-1)
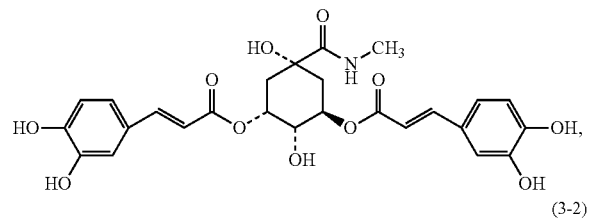

(3-2)
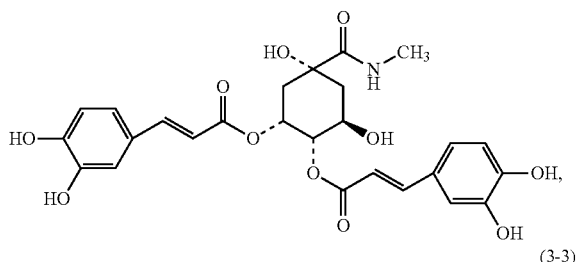

(3-3)
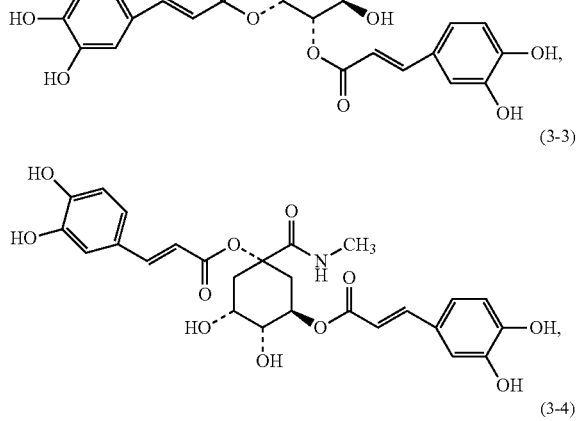

(3-4)

(3-5)
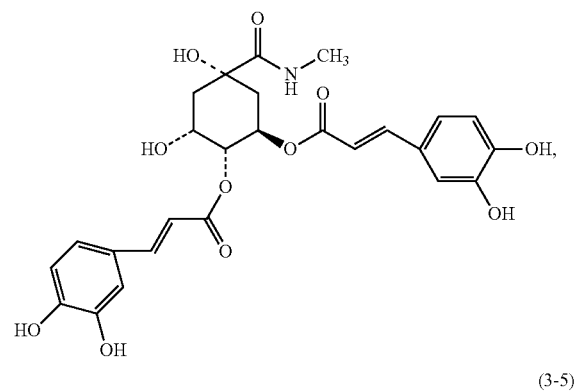

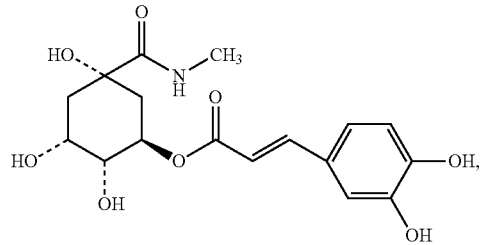

(3-6)
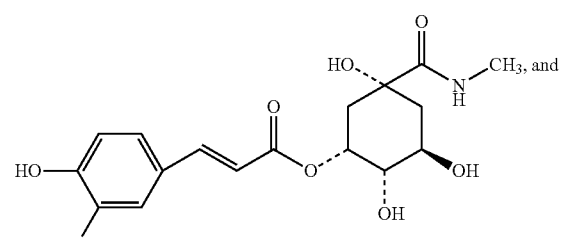

(3-7)
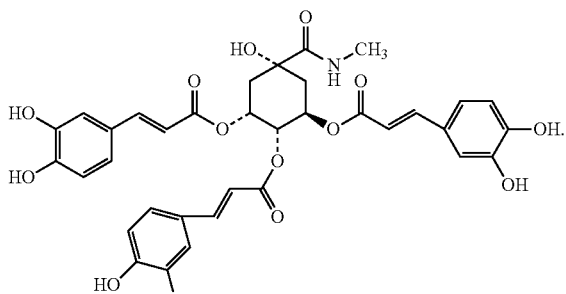

4. The compound of Formula (I) of claim 1, wherein two of $Q_1$, $Q_2$, $Q_3$ and $Q_4$ are H and two of $Q_1$, $Q_2$, $Q_3$ and $Q_4$ are the group of Formula (II).

5. The compound of Formula (I) of claim 1, wherein three of $Q_1$, $Q_2$, $Q_3$ and $Q_4$ are H and one of $Q_1$, $Q_2$, $Q_3$ and $Q_4$ is the group of Formula (II).

6. The compound of Formula (I) of claim 1, wherein one of $Q_1$, $Q_2$, $Q_3$ and $Q_4$ is H and three of $Q_1$, $Q_2$, $Q_3$ and $Q_4$ are the group of Formula (II).

7. A pharmaceutical composition consisting of a therapeutically effective amount of at least one compound according to claim 1 and pharmaceutically acceptable carriers or excipients.

8. A pharmaceutical composition consisting of a therapeutically effective amount of at least one compound according to claim 2 and pharmaceutically acceptable carriers or excipients.

9. A pharmaceutical composition consisting of a therapeutically effective amount of at least one compound according to claim 3 and pharmaceutically acceptable carriers or excipients.

10. The pharmaceutical composition according to claim 7, wherein the carrier is chosen from the group consisting of tablet, capsule, pill, oral liquid preparation, granule, powder, injection, implant, and external preparation.

11. The pharmaceutical composition according to claim 8, wherein the carrier is chosen from the group consisting of tablet, capsule, pill, oral liquid preparation, granule, powder, injection, implant, and external preparation.

12. The pharmaceutical composition according to claim 9, wherein the carrier is chosen from the group consisting of tablet, capsule, pill, oral liquid preparation, granule, powder, injection, implant, and external preparation.

13. A pharmaceutical composition for treatment of viral diseases comprising a therapeutically effective amount of at least one compound according to claim 1 and pharmaceutically acceptable carriers or excipients, wherein the viruses are respiratory syncytial virus, HIV-1 or hepatitis B virus.

14. A pharmaceutical composition for treatment of viral diseases comprising a therapeutically effective amount of at least one compound according to claim 2 and pharmaceutically acceptable carriers or excipients, wherein the viruses are respiratory syncytial virus, HIV-1 or hepatitis B virus.

15. A pharmaceutical composition for treatment of viral diseases comprising a therapeutically effective amount of at least one compound according to claim 3 and pharmaceutically acceptable carriers or excipients, wherein the viruses are respiratory syncytial virus, HIV-1 or hepatitis B virus.

16. A method of preparing a compound having a formula according to claim 3, wherein the compound is (1-1), (1-3), (1-4), (1-5), (2-1), (2-3), (2-4), (2-5), (3-1), (3-3), (3-4) or (3-5), and wherein the method comprises the steps of:

Step (1) reacting quinic acid of Formula 4 with cyclopentanone under catalysis of TsOH by refluxing with toluene to obtain a compound of Formula 5;

Step (2)
adding amine RH to a solution of compound of Formula 5 in THF and refluxing the mixture to obtain an amide of Formula 6, 7, or 8,

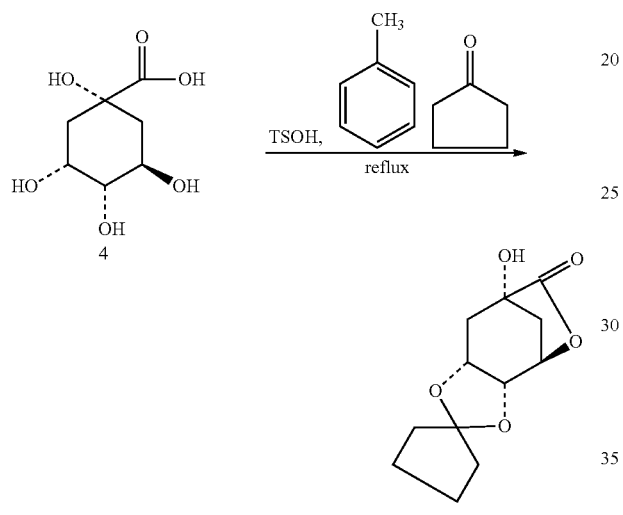

wherein, R is a cyclopropyl amino group, pyrrolidinyl group or methylamino group;

Step (3) reacting the amide compound of Formula 6, 7, and 8 with 1M HCl and MeOH at room temperature to provide compounds of Formula 9, 10, and 11, respectively;

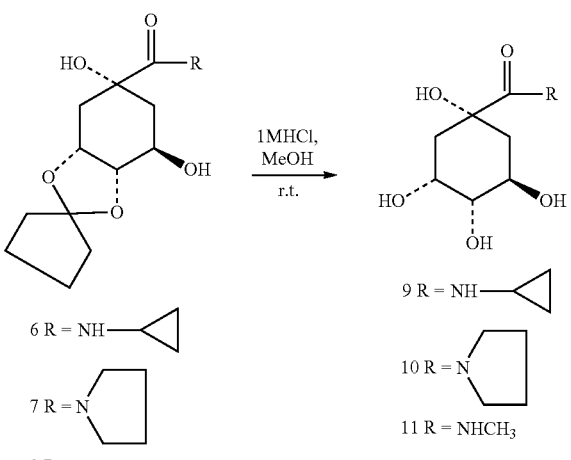

Step (4) esterifying the compound of Formula 9, 10, and 11 with O-allyl caffeoyl chloride in dichloromethane, in the presence of pyridine, at 0~5° C. to provide a compound of Formula 12, 13, or 14, 15, 16, or 17, and 18, 19, or 20 respectively;

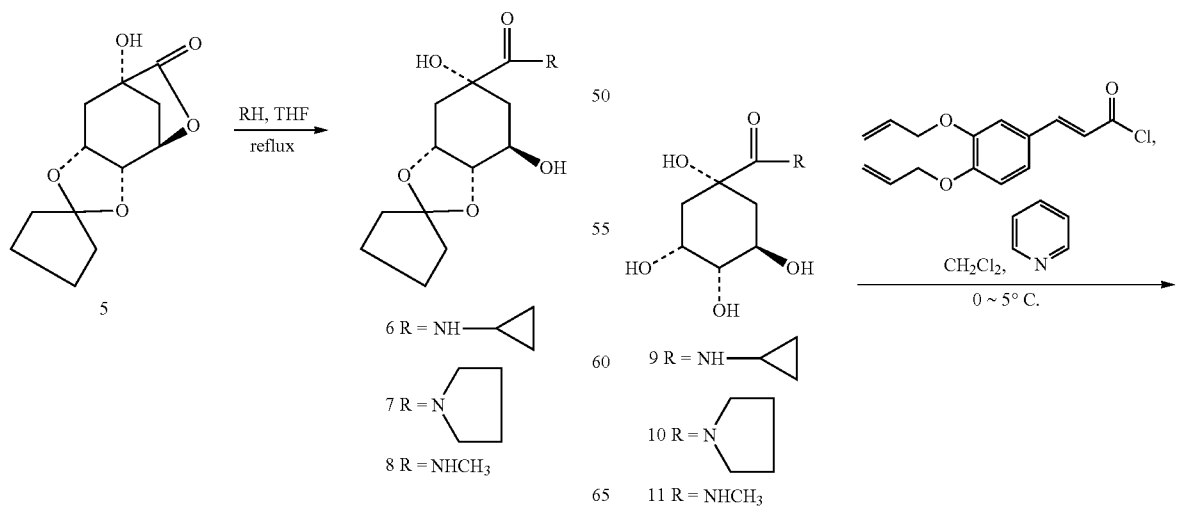

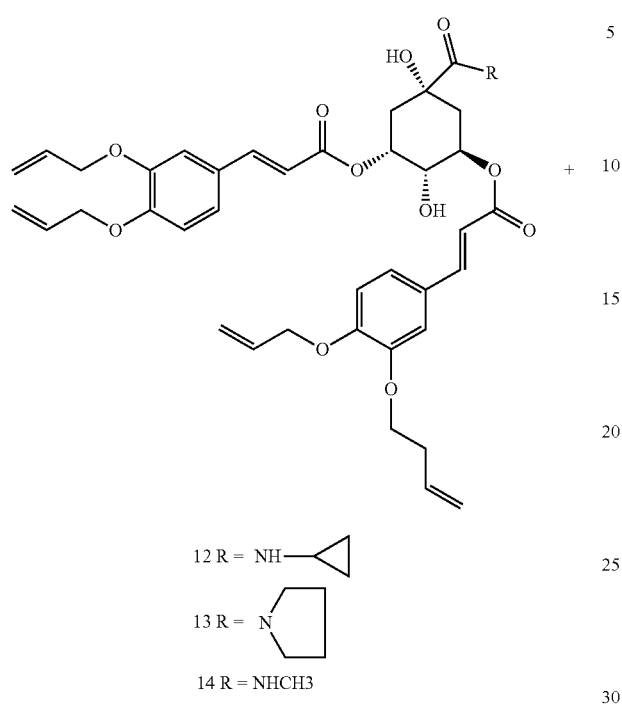
12 R = NH—cyclopropyl
13 R = N-pyrrolidinyl
14 R = NHCH3
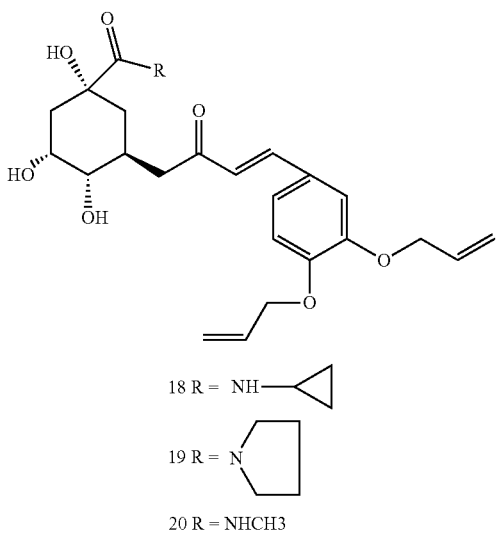
18 R = NH—cyclopropyl
19 R = N-pyrrolidinyl
20 R = NHCH3
Step (5) reacting the compound of Formula 12, 13, or 14, 15, 16, or 17, and 18, 19, or 20, with Pd(PPH$_3$)$_4$/Morpholine/THF to provide the compound of Formula (I)
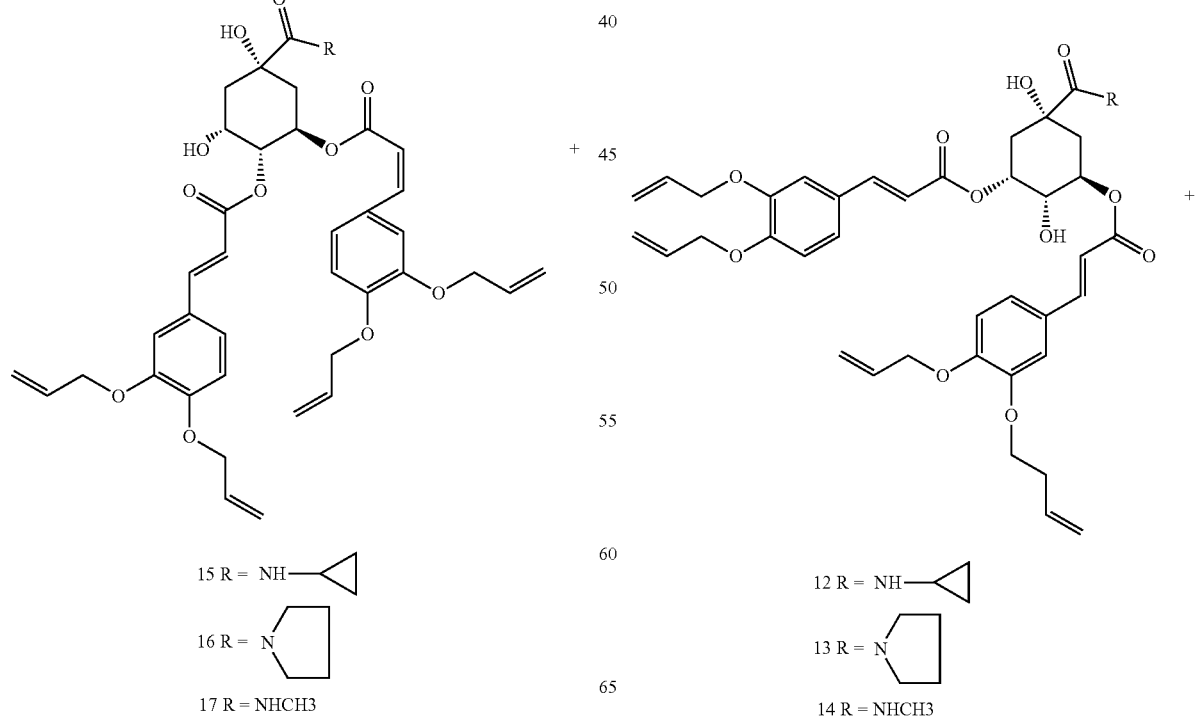
15 R = NH—cyclopropyl
16 R = N-pyrrolidinyl
17 R = NHCH3
12 R = NH—cyclopropyl
13 R = N-pyrrolidinyl
14 R = NHCH3

-continued

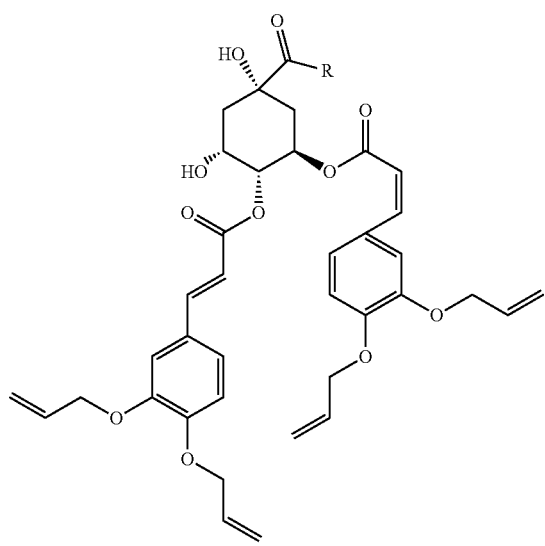

15 R = NH—⊲
16 R = N⊃
17 R = NHCH3

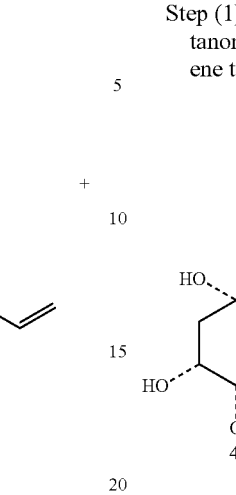

18 R = NH—⊲
19 R = N⊃
20 R = NHCH3

(I)

wherein the compound of Formula (I) represents the compounds (1-1), (1-4), (1-5), (2-1), (2-4), (2-5), (3-1), (3-4), (3-5) of claim 3;

or:

Step (1) reacting quinic acid of Formula 4 with cyclopentanone under catalysis of TsOH by refluxing with toluene to obtain compound of Formula 5;

Step (2) adding amine RH to a solution of compound of Formula 5 in THF and refluxing the mixture to obtain an amide of Formula 6, 7, or 8, wherein, R is a cyclopropyl amino group, pyrrolidinyl group or methylamino group;

Step (3) esterifying the compound of Formula 6, 7, and 8 with DMAP in dichloromethane, in the presence of pyridine, at room temperature to provide a compound of Formula 21, 22, and 23, respectively;

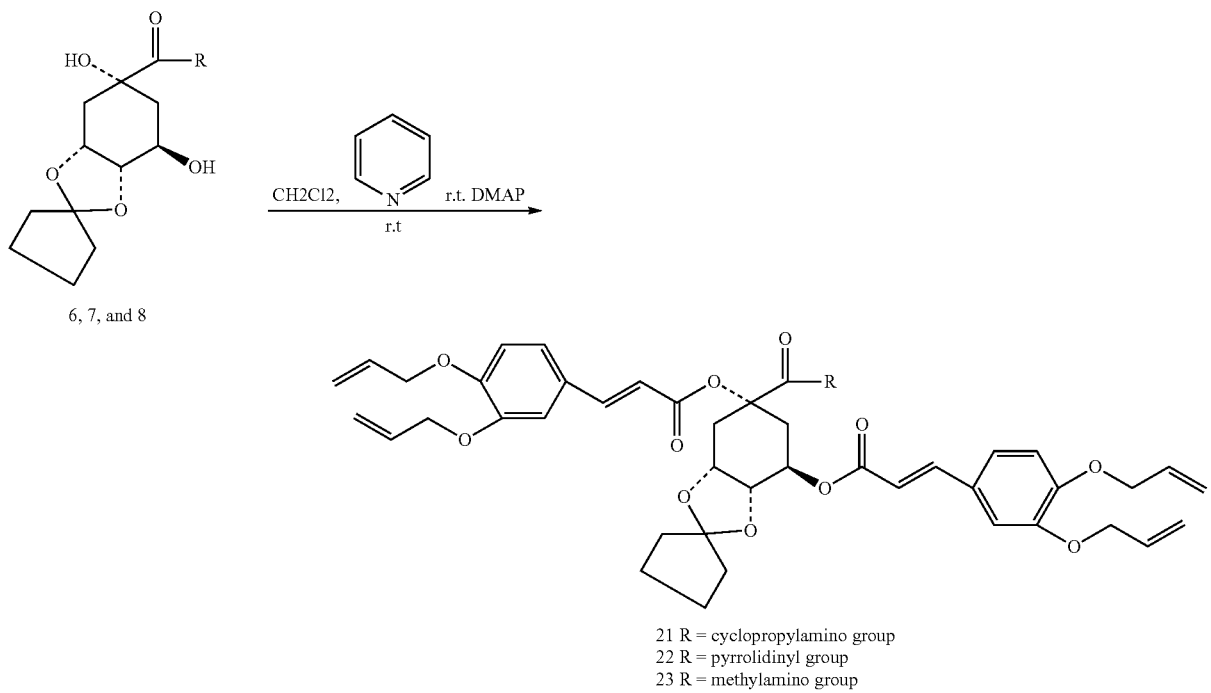
6, 7, and 8
21 R = cyclopropylamino group
22 R = pyrrolidinyl group
23 R = methylamino group
Step (4) adjusting the pH of the compound of Formula 21, 22, and 23 with HCl and stirring at room temperature to provide compound of Formula (I);
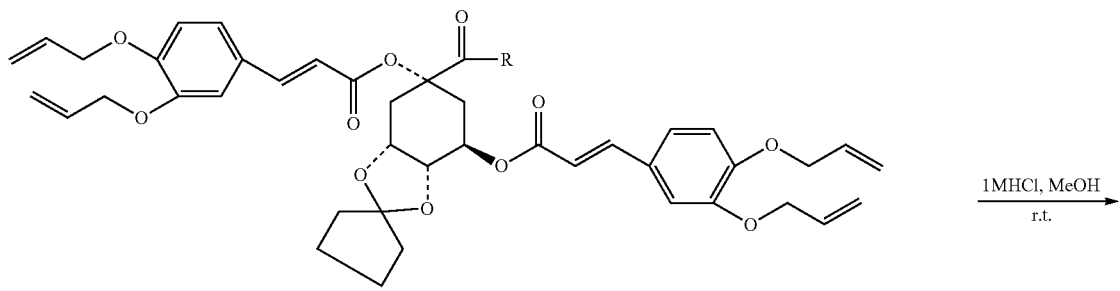
21 R = cyclopropylamino group
22 R = pyrrolidinyl group
23 R = methylamino group
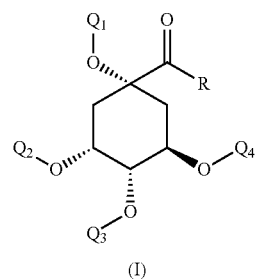
(I)
wherein, the compound of Formula (I) represents the compounds (1-3), (2-3), and (3-3) of claim 3.
* * * * *